US006562571B1

United States Patent
Wu et al.

(10) Patent No.: US 6,562,571 B1
(45) Date of Patent: May 13, 2003

(54) HUMAN HEME-REGULATED INITIATION FACTOR 2-α KINASE

(75) Inventors: J. H. David Wu, Pittsford, NY (US); Takeshi Omasa, Hyogo (JP); Athanassios Mantalaris, Harrow (GB); Yi-Guang Chen, Rochester, NY (US); Ying-Chuech Tsai, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/578,441

(22) Filed: May 25, 2000

Related U.S. Application Data

(60) Provisional application No. 60/135,713, filed on May 25, 1999.

(51) Int. Cl.$^7$ ............... C12Q 1/68; C07H 21/04; C07H 21/02; C12N 5/00; C12N 15/00
(52) U.S. Cl. ............ 435/6; 435/325; 435/320.1; 536/23.1; 536/24.3; 536/24.32
(58) Field of Search ............... 536/23.1, 23.4, 536/24.3, 24.32, 24.33; 435/6, 325, 320.1

(56) References Cited

U.S. PATENT DOCUMENTS

| | | | |
|---|---|---|---|
| 5,525,513 A | * 6/1996 | Chen et al. | 435/320.1 |
| 5,580,747 A | 12/1996 | Shulz et al. | 435/24 |
| 5,670,330 A | 9/1997 | Sonenberg et al. | 435/15 |
| 5,690,930 A | * 11/1997 | Chen et al. | 424/94.5 |
| 5,738,985 A | 4/1998 | Miles et al. | 435/5 |
| 5,885,820 A | 3/1999 | Chang | 435/212 |
| 5,888,796 A | 3/1999 | Chang | 435/212 |

OTHER PUBLICATIONS

Berlanga et al. Journal of Biological Sciences vol. 273, No. 48 pp. 32340–32396, Nov. 1991.*
Chen et al., "Amino Acid Microsequencing of Internal Tryptic Peptides of Heme–Regulated Eukaryotic Initiation Factor 2α Subunit Kinase: Homology to Protein Kinases," *Proc. Nat'l. Acad. Sci. USA* 88(2):315–319 (1991).
Hanks et al., "The Protein Kinase Family: Conserved Features and Deduced Phylogeny of the Catalytic Domains," *Science* 241(4861):42–52 (1988).
Pal et al., "Tissue Distribution and Immunoreactivity of Heme–Regulated eIF–2α Kinase Determined by Monoclonal Antibodies," *Biochemistry* 30(9):2555–2562 (1991).
Beretta et al., "Expression of the Protein Kinase PKR is Modulated by IRF–1 and is Reduced in 5q– Associated Leukemias," *Oncogene* 12(7):1593–1596 (1996).
Raught et al., "Expression of a Translationally Regulated, Dominant–Negative CCAAT/Enhancer–Binding Protein β Isoform and Up–Regulation of the Eukaryotic Translation Initiation Factor 2α are Correlated with Neoplastic Transformation of Mammary Epithelial Cells," *Cancer Res.* 56(19):4382–4386 (1996).
Uma et al., "Changes in the Expression of the Heme–Regulated eIF–2α Kinase and Heat Shock Proteins in Rabbit Reticulocytes Maturing During Recovery from Anemia," *Exp. Cell Res.* 238(1):273–282 (1998).
Der et al., "A Double–Stranded RNA–Activated Protein Kinase–Dependent Pathway Mediating Stress–Induced Apoptosis," *Proc. Natl. Acad. Sci. USA* 94(7):3279–3283 (1997).
Kumar et al., "Deficient Cytokine Signaling in Mouse Embryo Fibroblasts with a Targeted Deletion in the PKR Gene: Role of IRF–1 and NF–κB," *EMBO J.*, 16(2):406–416 (1997).
Chefalo et al., "Heme–Regulated eIF–2α Kinase Purifies as a Hemoprotein.," *Eur. J. Biochem.*, 258(2):820–830 (1998).
Berlanga et al., "Characterization of the Hemin–Sensitive Eukaryotic Initiation Factor 2α Kinase from Mouse Non-erythroid Cells," *J Biol. Chem.*, 273(48):32340–32346 (1998).

* cited by examiner

*Primary Examiner*—Kenneth R. Horlick
*Assistant Examiner*—Cynthia Wilder
(74) *Attorney, Agent, or Firm*—Nixon Peabody LLP

(57) ABSTRACT

The present invention provides an isolated nucleic acid sequence encoding a human heme-regulated initiation factor 2 alpha kinase. In addition, the invention provides a method for inhibiting protein synthesis, inducing cellular differentiation, or inhibiting infection in human cells by administering an effective amount of a heme-regulated initiation factor 2 alpha kinase to the cells. Methods are also provided for for modulating heme-regulated initiation factor 2 alpha kinase activity and determining the level of heme-regulated initiation factor 2 alpha kinase expression.

11 Claims, 1 Drawing Sheet

```
Human    1 MQGGNSGVRK REEEGDGAGA VAA---PPAIDFP AEGPDPEYDE SDVPAEIQVL KEPLQQPTFP
MOUSE    1 MLGGSSVDGE RDTDDDAAGA VAA---PPAIDFP AEVSDPKYDE SDVPAELQVL KEPLQQPTFP
RAT      1 MLGGGSVDGE RDTDDDAAGA VAA---PPAIDFP AEVSDPKYDE SDVPAELQVF KEPLQQPTFP
RABBIT   1 MLGGSAGTRG GEAEGDGAGA VGAVAPPPAIDFP AEVSDPKYDE SDVPAELQVL KEPLQQPAFP Human   61 FAVANQLLLV SLLEHLSHVH EPNPLRSRQV FKLLCQTFIK MGLLSSFTCS DEFSSLRLHH
MOUSE   61 FLVANQLLLV SLLEHLSHVH EPNPLHSKQV FKLLCQTFIK MGLLSSFTCS DEFSSLRLHH
RAT     61 FLVANQLLLV SLLEHLSHVH EPNPLHSKQV FKLLCQTFIK MGLLSSFTCS DEFSSLRLHH
RABBIT  64 FAVANQLLLV SLLEHLSHVH EPNPLRSRQV FKLLCQTFIK MGLLSSFTCS DEFSSLRLHH
                                                                          I
Human  121 NRAITHLMRS AKERVRQDPC EDISRIQKIR SREVALEAQT SRYLNEFEEL AILGKGGYGR
MOUSE  121 NRAITHLMRS AKERVRQDPC QDNSYMQKIR SREIAFEAQT SRYLNEFEEL AILGKGGYGR
RAT    121 NRAITHLMRS AKERVRQDPC QDNSYMQKIR SREIALEAQT SRYLNEFEEL AILGKGGYGR
RABBIT 124 NRAITHLMRS ARERVRQDPC ADNSHIQKIR SREVALEAQT SRYLNEFEEL SILGKGGYGR
                    II                  III                  IV
Human  181 VYKVRNKLDG QYYAIKKILI KGATKPVCMK VLRKVKVLAG LQHPNIVGYH TAWIEHVHVI
MOUSE  181 VYKVRNKLDG QHYAIKKILI KSATKTDCMK VLREVKVLAG LQHPNIVGYH TAWIEHVHVV
RAT    181 VYKVRNKLDG QHYAIKKILI KSATKTDCMK VLREVKVLAG LQHPNIVGYH TAWIEHVHVL
RABBIT 184 VYKVRNKLDG QYYAIKKILI KGATKTDCMK VLREVKVLAG LQHPNIVGYH TAWIEHVHVH Human  241 QPRDRAAIEL PSLEVLSDQE EDREQCGVKNDESSSSSIIFA EPTPEKEKRF GESDTENQNN
MOUSE  241 QPQDRVPIQL PSLEVLSEQE GDRDQGGVK-DNESSSSIVFA ELTPEKEKPF GESEVKNENN
RAT    241 QPQDRVPIQL PSLEVLSEHE GDRNQGGVK-DNESSSSIIFA ELTPEKENPL AESDVKNENN
RABBIT 244 VQADRVPIQL PSLEVLSDQE EDRDQYGVKNDASSSSSIIFA EFSPEKEKSS DECAVESQNN Human  302 KSVKYTTNLV IRESGELEST LELQENGLAG LSASSIVEQQ LPLRRNSHLE ESFTSTEESS
MOUSE  301 NLVSYTANLV VRNSSESESS IELQEDGLTD LSVRPVVRHQ LPLGHSSELE GNFTSTDESS
RAT    301 NLVSYRANLV IRSSSESESS IELQEDGLNE SPLRPVVKHQ LPLGHSSDVE GNFTSTDESS
RABBIT 305 KLVNYTTNLV VRDTGEFESS TERQENG--- ----SIVERQ LLFGHNSDVE EDFTSAEESS
                                            V                        HRM1
Human  362 EENVNFLGQT EAQYHLMLHI QMQLCELSLW DWIVERNKRG REYVDESACP YVMANVATKI
MOUSE  361 EGNLNLLGQT DVRYHLMLHI QMQLCELSLW DWITERNKRS REYVDEAACP YVMASVATKI
RAT    361 EDNLNLLGQT EARYHLMLHI QMQLCELSLW DWIAERNKRS RKCVDEAACP YVMASVATKI
RABBIT 358 EEDLSALRHT EVQYHLMLHI QMQLCELSLW DWIAERNRRS RECVDESACP YVMVSVATKI
                 VIa                 VIb                  VII
Human  422 FQELVEGVFY IHNMGIVHRD LKPRNIFLHG PDQQVKIGDF GLACTDILQK NTDWTRNGK
MOUSE  421 FQELVEGVFY IHNMGIVHRD LKPRNIFLHG PDQQVKIGDF GLACADIIQ- NADWTNRNGK
RAT    421 FQELVEGVFY IHNMGIVHRD LKPRNIFLHG PDQQVKIGDF GLACADIIQK SADWTNRNGK
RABBIT 418 FQELVEGVFY IHNMGIVHRD LKPRNIFLHG PDQQVKIGDF GLACADIIQK NAARTSRNGE
                    VIII                                IX
Human  482 RTPTHTSRVG TCLYASPEQL EGSEYDAKSD MYSLGVVLLE LFQPFGTEME RAEVLTGLRT
MOUSE  480 GTRTHTSRVG TCLYASPEQL EGSQYDAKSD MYSLGVILLE LFQPFGTEME RATVLTGVRT
RAT    481 GTPTHTSRVG TCLYASPEQL EGSEYDAKSD MYSLGVILLE LFQPFGTEME RATVLTGVRT
RABBIT 478 RAPTHTSRVG TCLYASPEQL EGSEYDAKSD MYSVGVILLE LFQPFGTEME RAEVLTGVRA
                 X       HRM2                 XI
Human  542 GQLPESLRKR CPVQAKYIQH LTRRNSSQRP SAIQLLQSEL FQNSGNVNLT LQMKDNRARK
MOUSE  540 GRIPESLSKR CPVQAKYIQL LTGRNVSQRP SALQLLQSEL FQTTGNVNLT LQMKIIEQEK
RAT    541 GRIPESLSKR CPVQAKYIQL LTGRNAAQRP SALQLLQSEL FQTTGNVNLT LQMKIMEQEK
RABBIT 538 GRIPDSLSKR CPAQAKYVQL LTRRNASQRP SALQLLQSEL FQNSAHVNLT LQMKIIEQER Human  602 RNCRTKEAAK PPFSRQRGEG              HRM...Hem regulatory motif
MOUSE  600 EIEELKKQLS LLSQDRGLKR              I...XI  kinase subdomains
RAT    601 EIEELKKQLS LLSQDKGLKR                      622 AA
RABBIT 598 EIEELKKQLS LLSQARGVRS DRRDGELPA
```

COMPARISON BETWEEN HUMAN, MOUSE, RAT, AND RABBIT HRI

SEQUENCE LISTING

<160> NUMBER OF SEQ ID NOS: 5

<210> SEQ ID NO 1
<211> LENGTH: 2891
<212> TYPE: DNA
<213> ORGANISM: Homo sapiens

<400> SEQUENCE: 1

```
ggcacgaggc tagctgcagc atcggagtgt gcagtgctgg gctggccggc gggctgggct      60
gcggcccgcg cgcggccggc gatgcagggg ggcaactccg gggtccgcaa gcgcgaagag     120
gagggcgacg gggctggggc tgtggctgcg ccgccggcca tcgactttcc cgccgagggc     180
ccggaccccg aatatgacga atctgatgtt ccagcagaaa tccaggtgtt aaaagaaccc     240
ctacaacagc caaccttccc ttttgcagtt gcaaaccaac tcttgctggt ttctttgctg     300
gagcacttga gccacgtgca tgaaccaaac ccacttcgtt caagacaggt gtttaagcta     360
ctttgccaga cgtttatcaa aatggggctg ctgtcttctt tcacttgtag tgacgagttt     420
agctcattga gactacatca caacagagct attactcact taatgaggtc tgctaaagag     480
agagttcgtc aggatccttg tgaggatatt tctcgtatcc agaaaatcag atcaagggaa     540
gtagccttgg aagcacaaac ttcacgttac ttaaatgaat ttgaagaact tgccatctta     600
ggaaaaggtg gatacggaag agtatacaag gtcaggaata aattagatgg tcagtattat     660
gcaataaaaa aaatcctgat taagggtgca actaaaccag tttgcatgaa ggtcctacgg     720
gaagtgaagg tgctggcagg tcttcagcac cccaatattg ttggctatca caccgcgtgg     780
atagaacatg ttcatgtgat tcagccacga gacagagctg ccattgagtt gccatctctg     840
gaagtgctct ccgaccagga agaggacaga gagcaatgtg gtgttaaaaa tgatgaaagt     900
agcagctcat ccattatctt tgctgagccc accccagaaa aagaaaaacg ctttggagaa     960
tctgacactg aaaatcagaa taacaagtcg gtgaagtaca ccaccaattt agtcataaga    1020
```

-continued

```
gaatctggtg aacttgagtc gaccctggag ctccaggaaa atggcttggc tggtttgtct      1080
gccagttcaa ttgtggaaca gcagctgcca ctcaggcgta attcccacct agaggagagt      1140
ttcacatcca ccgaagaatc ttccgaagaa aatgtcaact ttttgggtca gacagaggca      1200
cagtaccacc tgatgctgca catccagatg cagctgtgtg agctctcgct gtgggattgg      1260
atagtcgaga gaaacaagcg gggccgggag tatgtggacg agtctgcctg tccttatgtt      1320
atggccaatg ttgcaacaaa aattttttcaa gaattggtag aaggtgtgtt ttacatacat      1380
aacatgggaa ttgtgcaccg agatctgaag ccaagaaata tttttcttca tggccctgat      1440
cagcaagtaa aataggaga ctttggtctg gcctgcacag acatcctaca gaagaacaca      1500
gactggacca acagaaacgg gaagagaaca ccaacacata cgtccagagt gggtacttgt      1560
ctgtacgctt cacccgaaca gttggaagga tctgagtatg atgccaagtc agatatgtac      1620
agcttgggtg tggtcctgct agagctcttt cagccgtttg aacagaaaat ggagcgagca      1680
gaagttctaa caggtttaag aactggtcag ttgccggaat ccctccgtaa aaggtgtcca      1740
gtgcaagcca agtatatcca gcacttaacg agaaggaact catcgcagag accatctgcc      1800
attcagctgc tgcagagtga acttttccaa aattctggaa atgttaacct caccctacag      1860
atgaagataa tagagcaaga aaaagaaatt gcagaactaa agaagcagct aaacctcctt      1920
tctcaagaca aggggtgagg ggatgacgga aaggatgggg gcgtgggatg aaagtggact      1980
taacttttaa ggtagttaac tggaatgtaa atttttaatc tttattaggg tatagttggt      2040
acaatgcttc gttgtattta gtaagccttt acaagacttg ttaaagatgt cagagtgccc      2100
caagctgccg ttccttccct tcctgcccca caagctcctt ttcctgaatt tcctacctaa      2160
atattaacca tatgcctagt ctctgaaact aaaaacttgg acctcatcct caattatttt      2220
ctcctttcaa ctctgttgac cctctgtctg gtcttcctct agaaggttct accgcagaaa      2280
ttgatgtgtg ctccctgccc tcgtcactgc ccaagcccgg gcctgcacat actcactgga      2340
ctgttccagt tttgacagct gccagtcttc ctgcccettt cacactgcag ctgaagttca      2400
ttacctgaag gacgcctcat catttcattc cttggctcca aaccttctgc tgcctctaag      2460
ataaaagctc aacttcttaa cagtgtacag tgtgcaactt ccaacctttt tatctgttct      2520
ctccaccttc agtttagcgt cattccaaaa ccacaccctt gcaaagcttt gtactccgca      2580
ccccagatga tctccaggca gctcagatct ctttcctgcc tttgccctgc actgttcccc      2640
ggtacttcct cctttattgt agcactcagc tccccagcca atctgtacat ccctcagagg      2700
cagcgatctg atgaattggt ttttgaatcc cagaaagggt ctgccatgga gttggcagtc      2760
atcacggtag atggcgtatg attttgctga attttaaata aaatgaaaac cataaattac      2820
atgatgcttt tattgacact tgacaactgg cctaaataaa aagactctga ctctaaaaaa      2880 aaaaaaaaa a                                                            2891
```

<210> SEQ ID NO 2
<211> LENGTH: 629
<212> TYPE: PRT
<213> ORGANISM: Homo sapiens

<400> SEQUENCE: 2

Met Gln Gly Gly Asn Ser Gly Val Arg Lys Arg Glu Glu Glu Gly Asp
1               5                   10                  15

Gly Ala Gly Ala Val Ala Ala Pro Pro Ala Ile Asp Phe Pro Ala Glu
            20                  25                  30

```
Gly Pro Asp Pro Glu Tyr Asp Glu Ser Asp Val Pro Ala Glu Ile Gln
         35                  40                  45

Val Leu Lys Glu Pro Leu Gln Gln Pro Thr Phe Pro Phe Ala Val Ala
         50                  55                  60

Asn Gln Leu Leu Leu Val Ser Leu Leu Glu His Leu Ser His Val His
 65                  70                  75                  80

Glu Pro Asn Pro Leu Arg Ser Arg Gln Val Phe Lys Leu Leu Cys Gln
                 85                  90                  95

Thr Phe Ile Lys Met Gly Leu Leu Ser Ser Phe Thr Cys Ser Asp Glu
            100                 105                 110

Phe Ser Ser Leu Arg Leu His His Asn Arg Ala Ile Thr His Leu Met
        115                 120                 125

Arg Ser Ala Lys Glu Arg Val Arg Gln Asp Pro Cys Glu Asp Ile Ser
    130                 135                 140

Arg Ile Gln Lys Ile Arg Ser Arg Glu Val Ala Leu Glu Ala Gln Thr
145                 150                 155                 160

Ser Arg Tyr Leu Asn Glu Phe Glu Glu Leu Ala Ile Leu Gly Lys Gly
                165                 170                 175

Gly Tyr Gly Arg Val Tyr Lys Val Arg Asn Lys Leu Asp Gly Gln Tyr
            180                 185                 190

Tyr Ala Ile Lys Lys Ile Leu Ile Lys Gly Ala Thr Lys Pro Val Cys
        195                 200                 205

Met Lys Val Leu Arg Glu Val Lys Val Leu Ala Gly Leu Gln His Pro
    210                 215                 220

Asn Ile Val Gly Tyr His Thr Ala Trp Ile Glu His Val His Val Ile
225                 230                 235                 240

Gln Pro Arg Asp Arg Ala Ala Ile Glu Leu Pro Ser Leu Glu Val Leu
                245                 250                 255

Ser Asp Gln Glu Glu Asp Arg Glu Gln Cys Gly Val Lys Asn Asp Glu
            260                 265                 270

Ser Ser Ser Ser Ser Ile Ile Phe Ala Glu Pro Thr Pro Glu Lys Glu
        275                 280                 285

Lys Arg Phe Gly Glu Ser Asp Thr Glu Asn Gln Asn Asn Lys Ser Val
    290                 295                 300

Lys Tyr Thr Thr Asn Leu Val Ile Arg Glu Ser Gly Glu Leu Glu Ser
305                 310                 315                 320

Thr Leu Glu Leu Gln Glu Asn Gly Leu Ala Gly Leu Ser Ala Ser Ser
                325                 330                 335

Ile Val Glu Gln Gln Leu Pro Leu Arg Arg Asn Ser His Leu Glu Glu
            340                 345                 350

Ser Phe Thr Ser Thr Glu Glu Ser Glu Glu Asn Val Asn Phe Leu
        355                 360                 365

Gly Gln Thr Glu Ala Gln Tyr His Leu Met Leu His Ile Gln Met Gln
    370                 375                 380

Leu Cys Glu Leu Ser Leu Trp Asp Trp Ile Val Glu Arg Asn Lys Arg
385                 390                 395                 400

Gly Arg Glu Tyr Val Asp Glu Ser Ala Cys Pro Tyr Val Met Ala Asn
                405                 410                 415

Val Ala Thr Lys Ile Phe Gln Glu Leu Val Glu Gly Val Phe Tyr Ile
            420                 425                 430

His Asn Met Gly Ile Val His Arg Asp Leu Lys Pro Arg Asn Ile Phe
        435                 440                 445

Leu His Gly Pro Asp Gln Gln Val Lys Ile Gly Asp Phe Gly Leu Ala
```

```
                    450                 455                 460
Cys Thr Asp Ile Leu Gln Lys Asn Thr Asp Trp Thr Asn Arg Asn Gly
465                 470                 475                 480

Lys Arg Thr Pro Thr His Thr Ser Arg Val Gly Thr Cys Leu Tyr Ala
                    485                 490                 495

Ser Pro Glu Gln Leu Glu Gly Ser Glu Tyr Asp Ala Lys Ser Asp Met
                500                 505                 510

Tyr Ser Leu Gly Val Val Leu Leu Glu Leu Phe Gln Pro Phe Gly Thr
            515                 520                 525

Glu Met Glu Arg Ala Glu Val Leu Thr Gly Leu Arg Thr Gly Gln Leu
        530                 535                 540

Pro Glu Ser Leu Arg Lys Arg Cys Pro Val Gln Ala Lys Tyr Ile Gln
545                 550                 555                 560

His Leu Thr Arg Arg Asn Ser Ser Gln Arg Pro Ser Ala Ile Gln Leu
                565                 570                 575

Leu Gln Ser Glu Leu Phe Gln Asn Ser Gly Asn Val Asn Leu Thr Leu
                580                 585                 590

Gln Met Lys Ile Ile Glu Gln Glu Lys Glu Ile Ala Glu Leu Lys Lys
            595                 600                 605

Gln Leu Asn Leu Leu Ser Gln Asp Lys Gly Val Arg Asp Asp Gly Lys
        610                 615                 620

Asp Gly Gly Val Gly
625

<210> SEQ ID NO 3
<211> LENGTH: 619
<212> TYPE: PRT
<213> ORGANISM: Mus musculus

<400> SEQUENCE: 3

Met Leu Gly Gly Ser Ser Val Asp Gly Glu Arg Asp Thr Asp Asp Asp
 1               5                  10                  15

Ala Ala Gly Ala Val Ala Ala Pro Pro Ala Ile Asp Phe Pro Ala Glu
                20                  25                  30

Val Ser Asp Pro Lys Tyr Asp Glu Ser Asp Val Pro Ala Glu Leu Gln
            35                  40                  45

Val Leu Lys Glu Pro Leu Gln Gln Pro Thr Phe Pro Phe Leu Val Ala
        50                  55                  60

Asn Gln Leu Leu Leu Val Ser Leu Leu Glu His Leu Ser His Val His
65                  70                  75                  80

Glu Pro Asn Pro Leu His Ser Lys Gln Val Phe Lys Leu Leu Cys Gln
                85                  90                  95

Thr Phe Ile Lys Met Gly Leu Leu Ser Ser Phe Thr Cys Ser Asp Glu
                100                 105                 110

Phe Ser Ser Leu Arg Leu His His Asn Arg Ala Ile Thr His Leu Met
            115                 120                 125

Arg Ser Ala Lys Glu Arg Val Arg Gln Asp Pro Cys Gln Asp Asn Ser
        130                 135                 140

Tyr Met Gln Lys Ile Arg Ser Arg Glu Ile Ala Phe Glu Ala Gln Thr
145                 150                 155                 160

Ser Arg Tyr Leu Asn Glu Phe Glu Glu Leu Ala Ile Leu Gly Lys Gly
                165                 170                 175

Gly Tyr Gly Arg Val Tyr Lys Val Arg Asn Lys Leu Asp Gly Gln His
            180                 185                 190
```

-continued

```
Tyr Ala Ile Lys Lys Ile Leu Ile Lys Ser Ala Thr Lys Thr Asp Cys
        195                 200                 205

Met Lys Val Leu Arg Glu Val Lys Val Leu Ala Gly Leu Gln His Pro
        210                 215                 220

Asn Ile Val Gly Tyr His Thr Ala Trp Ile Glu His Val His Val Val
225                 230                 235                 240

Gln Pro Gln Asp Arg Val Pro Ile Gln Leu Pro Ser Leu Glu Val Leu
                245                 250                 255

Ser Glu Gln Glu Gly Asp Arg Asp Gln Gly Gly Val Lys Asp Asn Glu
            260                 265                 270

Ser Ser Ser Ser Ile Val Phe Ala Glu Leu Thr Pro Glu Lys Glu Lys
        275                 280                 285

Pro Phe Gly Glu Ser Glu Val Lys Asn Glu Asn Asn Asn Leu Val Ser
        290                 295                 300

Tyr Thr Ala Asn Leu Val Val Arg Asn Ser Ser Glu Ser Glu Ser Ser
305                 310                 315                 320

Ile Glu Leu Gln Glu Asp Gly Leu Thr Asp Leu Ser Val Arg Pro Val
                325                 330                 335

Val Arg His Gln Leu Pro Leu Gly His Ser Ser Glu Leu Glu Gly Asn
            340                 345                 350

Phe Thr Ser Thr Asp Glu Ser Ser Glu Gly Asn Leu Asn Leu Leu Gly
        355                 360                 365

Gln Thr Asp Val Arg Tyr His Leu Met Leu His Ile Gln Met Gln Leu
        370                 375                 380

Cys Glu Leu Ser Leu Trp Asp Trp Ile Thr Glu Arg Asn Lys Arg Ser
385                 390                 395                 400

Arg Glu Tyr Val Asp Glu Ala Ala Cys Pro Tyr Val Met Ala Ser Val
                405                 410                 415

Ala Thr Lys Ile Phe Gln Glu Leu Val Glu Gly Val Phe Tyr Ile His
            420                 425                 430

Asn Met Gly Ile Val His Arg Asp Leu Lys Pro Arg Asn Ile Phe Leu
        435                 440                 445

His Gly Pro Asp Gln Gln Val Lys Ile Gly Asp Phe Gly Leu Ala Cys
        450                 455                 460

Ala Asp Ile Ile Gln Asn Ala Asp Trp Thr Asn Arg Asn Gly Lys Gly
465                 470                 475                 480

Thr Arg Thr His Thr Ser Arg Val Gly Thr Cys Leu Tyr Ala Ser Pro
                485                 490                 495

Glu Gln Leu Glu Gly Ser Gln Tyr Asp Ala Lys Ser Asp Met Tyr Ser
            500                 505                 510

Leu Gly Val Ile Leu Leu Glu Leu Phe Gln Pro Phe Gly Thr Glu Met
        515                 520                 525

Glu Arg Ala Thr Val Leu Thr Gly Val Arg Thr Gly Arg Ile Pro Glu
        530                 535                 540

Ser Leu Ser Lys Arg Cys Pro Val Gln Ala Lys Tyr Ile Gln Leu Leu
545                 550                 555                 560

Thr Gly Arg Asn Val Ser Gln Arg Pro Ser Ala Leu Gln Leu Leu Gln
                565                 570                 575

Ser Glu Leu Phe Gln Thr Thr Gly Asn Val Asn Leu Thr Leu Gln Met
            580                 585                 590

Lys Ile Ile Glu Gln Glu Lys Glu Ile Glu Glu Leu Lys Lys Gln Leu
        595                 600                 605

Ser Leu Leu Ser Gln Asp Arg Gly Leu Lys Arg
```

```
                  610                 615

<210> SEQ ID NO 4
<211> LENGTH: 620
<212> TYPE: PRT
<213> ORGANISM: Rattus norvegicus

<400> SEQUENCE: 4

Met Leu Gly Gly Gly Ser Val Asp Gly Glu Arg Asp Thr Asp Asp Asp
  1               5                  10                  15

Ala Ala Gly Ala Val Ala Ala Pro Pro Ala Ile Asp Phe Pro Ala Glu
             20                  25                  30

Val Ser Asp Pro Lys Tyr Asp Glu Ser Asp Val Pro Ala Glu Leu Gln
         35                  40                  45

Val Phe Lys Glu Pro Leu Gln Gln Pro Thr Phe Pro Phe Leu Val Ala
     50                  55                  60

Asn Gln Leu Leu Leu Val Ser Leu Leu Glu His Leu Ser His Val His
 65                  70                  75                  80

Glu Pro Asn Pro Leu His Ser Lys Gln Val Phe Lys Leu Leu Cys Gln
                 85                  90                  95

Thr Phe Ile Lys Met Gly Leu Leu Ser Ser Phe Thr Cys Ser Asp Glu
            100                 105                 110

Phe Ser Ser Leu Arg Leu His His Asn Arg Ala Ile Thr His Leu Met
            115                 120                 125

Arg Ser Ala Lys Glu Arg Val Arg Gln Asp Pro Cys Gln Asp Asn Ser
        130                 135                 140

Tyr Met Gln Lys Ile Arg Ser Arg Glu Ile Ala Leu Glu Ala Gln Thr
145                 150                 155                 160

Ser Arg Tyr Leu Asn Glu Phe Glu Leu Ala Ile Leu Gly Lys Gly
                165                 170                 175

Gly Tyr Gly Arg Val Tyr Lys Val Arg Asn Lys Leu Asp Gly Gln His
            180                 185                 190

Tyr Ala Ile Lys Lys Ile Leu Ile Lys Ser Ala Thr Lys Thr Asp Cys
        195                 200                 205

Met Lys Val Leu Arg Glu Val Lys Val Leu Ala Gly Leu Gln His Pro
210                 215                 220

Asn Ile Val Gly Tyr His Thr Ala Trp Ile Glu His Val His Val Leu
225                 230                 235                 240

Gln Pro Gln Asp Arg Val Pro Ile Gln Leu Pro Ser Leu Glu Val Leu
                245                 250                 255

Ser Glu His Glu Gly Asp Arg Asn Gln Gly Gly Val Lys Asp Asn Glu
            260                 265                 270

Ser Ser Ser Ile Ile Phe Ala Glu Leu Thr Pro Glu Lys Glu Asn
        275                 280                 285

Pro Leu Ala Glu Ser Asp Val Lys Asn Glu Asn Asn Asn Leu Val Ser
    290                 295                 300

Tyr Arg Ala Asn Leu Val Ile Arg Ser Ser Glu Ser Glu Ser Ser
305                 310                 315                 320

Ile Glu Leu Gln Glu Asp Gly Leu Asn Glu Ser Pro Leu Arg Pro Val
                325                 330                 335

Val Lys His Gln Leu Pro Leu Gly His Ser Ser Asp Val Glu Gly Asn
            340                 345                 350

Phe Thr Ser Thr Asp Glu Ser Ser Glu Asp Asn Leu Asn Leu Leu Gly
        355                 360                 365
```

Gln Thr Glu Ala Arg Tyr His Leu Met Leu His Ile Gln Met Gln Leu
    370                 375                 380

Cys Glu Leu Ser Leu Trp Asp Trp Ile Ala Glu Arg Asn Lys Arg Ser
385                 390                 395                 400

Arg Lys Cys Val Asp Glu Ala Ala Cys Pro Tyr Val Met Ala Ser Val
                405                 410                 415

Ala Thr Lys Ile Phe Gln Glu Leu Val Glu Gly Val Phe Tyr Ile His
            420                 425                 430

Asn Met Gly Ile Val His Arg Asp Leu Lys Pro Arg Asn Ile Phe Leu
        435                 440                 445

His Gly Pro Asp Gln Gln Val Lys Ile Gly Asp Phe Gly Leu Ala Cys
    450                 455                 460

Ala Asp Ile Ile Gln Lys Ser Ala Asp Trp Thr Asn Arg Asn Gly Lys
465                 470                 475                 480

Gly Thr Pro Thr His Thr Ser Arg Val Gly Thr Cys Leu Tyr Ala Ser
                485                 490                 495

Pro Glu Gln Leu Glu Gly Ser Glu Tyr Asp Ala Lys Ser Asp Met Tyr
            500                 505                 510

Ser Leu Gly Val Ile Leu Leu Glu Leu Phe Gln Pro Phe Gly Thr Glu
        515                 520                 525

Met Glu Arg Ala Thr Val Leu Thr Gly Val Arg Thr Gly Arg Ile Pro
    530                 535                 540

Glu Ser Leu Ser Lys Arg Cys Pro Val Gln Ala Lys Tyr Ile Gln Leu
545                 550                 555                 560

Leu Thr Gly Arg Asn Ala Ala Gln Arg Pro Ser Ala Leu Gln Leu Leu
                565                 570                 575

Gln Ser Glu Leu Phe Gln Thr Thr Gly Asn Val Asn Leu Thr Leu Gln
            580                 585                 590

Met Lys Ile Met Glu Gln Glu Lys Glu Ile Glu Glu Leu Lys Lys Gln
        595                 600                 605

Leu Ser Leu Leu Ser Gln Asp Lys Gly Leu Lys Arg
    610                 615                 620

<210> SEQ ID NO 5
<211> LENGTH: 626
<212> TYPE: PRT
<213> ORGANISM: Oryctolagus cuniculus

<400> SEQUENCE: 5

Met Leu Gly Gly Ser Ala Gly Thr Arg Gly Gly Glu Ala Glu Gly Asp
  1               5                  10                  15

Gly Ala Gly Ala Val Gly Ala Val Ala Pro Pro Ala Ile Asp Phe
            20                  25                  30

Pro Ala Glu Val Ser Asp Pro Lys Tyr Asp Glu Ser Asp Val Pro Ala
        35                  40                  45

Glu Leu Gln Val Leu Lys Glu Pro Leu Gln Gln Pro Ala Phe Pro Phe
    50                  55                  60

Ala Val Ala Asn Gln Leu Leu Val Ser Leu Glu His Leu Ser
65                  70                  75                  80

His Val His Glu Pro Asn Pro Leu Arg Ser Arg Gln Val Phe Lys Leu
                85                  90                  95

Leu Cys Gln Thr Phe Ile Lys Met Gly Leu Leu Ser Ser Phe Thr Cys
            100                 105                 110

Ser Asp Glu Phe Ser Ser Leu Arg Leu His His Asn Arg Ala Ile Thr
        115                 120                 125

-continued

```
His Leu Met Arg Ser Ala Arg Glu Arg Val Arg Gln Asp Pro Cys Ala
    130                 135                 140
Asp Asn Ser His Ile Gln Lys Ile Arg Ser Arg Glu Val Ala Leu Glu
145                 150                 155                 160
Ala Gln Thr Ser Arg Tyr Leu Asn Glu Phe Glu Glu Leu Ser Ile Leu
                165                 170                 175
Gly Lys Gly Gly Tyr Gly Arg Val Tyr Lys Val Arg Asn Lys Leu Asp
            180                 185                 190
Gly Gln Tyr Tyr Ala Ile Lys Lys Ile Leu Ile Lys Gly Ala Thr Lys
        195                 200                 205
Thr Asp Cys Met Lys Val Leu Arg Glu Val Lys Val Leu Ala Gly Leu
    210                 215                 220
Gln His Pro Asn Ile Val Gly Tyr His Thr Ala Trp Ile Glu His Val
225                 230                 235                 240
His Val His Val Gln Ala Asp Arg Val Pro Ile Gln Leu Pro Ser Leu
                245                 250                 255
Glu Val Leu Ser Asp Gln Glu Glu Asp Arg Asp Gln Tyr Gly Val Lys
            260                 265                 270
Asn Asp Ala Ser Ser Ser Ser Ile Ile Phe Ala Glu Phe Ser Pro
        275                 280                 285
Glu Lys Glu Lys Ser Ser Asp Glu Cys Ala Val Glu Ser Gln Asn Asn
    290                 295                 300
Lys Leu Val Asn Tyr Thr Thr Asn Leu Val Val Arg Asp Thr Gly Glu
305                 310                 315                 320
Phe Glu Ser Ser Thr Glu Arg Gln Glu Asn Gly Ser Ile Val Glu Arg
                325                 330                 335
Gln Leu Leu Phe Gly His Asn Ser Asp Val Glu Glu Asp Phe Thr Ser
            340                 345                 350
Ala Glu Glu Ser Ser Glu Glu Asp Leu Ser Ala Leu Arg His Thr Glu
        355                 360                 365
Val Gln Tyr His Leu Met Leu His Ile Gln Met Gln Leu Cys Glu Leu
    370                 375                 380
Ser Leu Trp Asp Trp Ile Ala Glu Arg Asn Arg Arg Ser Arg Glu Cys
385                 390                 395                 400
Val Asp Glu Ser Ala Cys Pro Tyr Val Met Val Ser Val Ala Thr Lys
                405                 410                 415
Ile Phe Gln Glu Leu Val Glu Gly Val Phe Tyr Ile His Asn Met Gly
            420                 425                 430
Ile Val His Arg Asp Leu Lys Pro Arg Asn Ile Phe Leu His Gly Pro
        435                 440                 445
Asp Gln Gln Val Lys Ile Gly Asp Phe Gly Leu Ala Cys Ala Asp Ile
    450                 455                 460
Ile Gln Lys Asn Ala Ala Arg Thr Ser Arg Asn Gly Glu Arg Ala Pro
465                 470                 475                 480
Thr His Thr Ser Arg Val Gly Thr Cys Leu Tyr Ala Ser Pro Glu Gln
                485                 490                 495
Leu Glu Gly Ser Glu Tyr Asp Ala Lys Ser Asp Met Tyr Ser Val Gly
            500                 505                 510
Val Ile Leu Leu Glu Leu Phe Gln Pro Phe Gly Thr Glu Met Glu Arg
        515                 520                 525
Ala Glu Val Leu Thr Gly Val Arg Ala Gly Arg Ile Pro Asp Ser Leu
    530                 535                 540
```

-continued

```
Ser Lys Arg Cys Pro Ala Gln Ala Lys Tyr Val Gln Leu Leu Thr Arg
545                 550                 555                 560

Arg Asn Ala Ser Gln Arg Pro Ser Ala Leu Gln Leu Leu Gln Ser Glu
                565                 570                 575

Leu Phe Gln Asn Ser Ala His Val Asn Leu Thr Leu Gln Met Lys Ile
                580                 585                 590

Ile Glu Gln Glu Arg Glu Ile Glu Glu Leu Lys Lys Gln Leu Ser Leu
                595                 600                 605

Leu Ser Gln Ala Arg Gly Val Arg Ser Asp Arg Arg Asp Gly Glu Leu
                610                 615                 620

Pro Ala
625
```

HUMAN HEME-REGULATED INITIATION FACTOR 2-α KINASE

The present application claims the benefit of U.S. Provisional Patent application Serial No. 60/135,713, filed May 25, 1999.

The subject matter of this application was made with support from the United States Government under Grant No. BES-963 1670 from the National Science Foundation. The United States Government may retain certain rights.

BACKGROUND OF THE INVENTION

Heme controls the synthesis of protein in reticulocytes. In heme-deficiency, there is diminished initiation of protein synthesis. The principal mechanism of the inhibition of initiation of protein synthesis is the phosphorylation of the alpha -subunit of the eukaryotic initiation factor 2, eIF-2 alpha. In addition to heme-deficiency, oxidized glutathione (GSSG) and low levels of double stranded RNA inhibit initiation by promoting phosphorylation of eIF-2 alpha.

The translation of mRNA in eukaryotic cells occurs in the cytoplasm. In the first step of initiation, free 80 S ribosomes are in equilibrium with their 40 S and 60 S subunits. In the presence of eIF-3, 40 S subunits bind the eIF-3 and eIF-4C to form a 43 S ribosomal complex; the binding of eIF-3 and eIF-4C to the 40 S subunit inhibits the joining of the 60 S subunit.

In the next step, eIF-2 binds GTP and the initiator tRNA, Met-tRNA f, in a ternary complex. The binding by eIF-2 is specific for both guanine nucleotides and for Met-tRNA f. The ternary complex now binds to the 43 S ribosomal complex to form the 43 S preinitiation complex. The 43 S preinitiation complex binds mRNA in an ATP-dependent reaction in which eIF-4A, eIF-4B, and eIF-4F form a complex with the mRNA. The product of the binding of mRNA to the 43 S structure is bound close to the ribosome and the AUG initiator codon is downstream from the cap structure.

The joining of the 48 S preinitiation complex and the 60 S subunit is catalyzed by eIF-5 which has a ribosome-dependent GTPase activity. The joining reaction is accompanied by the release of the initiation factors eIF-3 and eIF-4C, eIF-2 is translocated to 60 S subunit as a binary complex, eIF2-GDP. The product of the joining reaction is the 80 S initiation complex. Formation of the active 80 S initiation complex is the final step in initiation. The Met-tRNA f is positioned in the P (peptidyl) site on the ribosome for the start of polypeptide elongation.

The sequence of steps in the process of initiation affords several opportunities for regulation. These include the recycling of eIF-2 after its release as the eIF-2-GDP complex; the formation of the ternary complex; and the relative affinities of mRNAs for eIF-2 and for eIF-4A, -4B, and -4F in determining the relative rates of translation of the mRNAs.

Heme-deficiency inhibited initiation of protein synthesis is characterized by a brief period of control linear synthesis, followed by an abrupt decline in this rate and by disaggregation of polyribosomes, associated with a decrease in the formation of the eIF-2-Met-tRNA f -GTP ternary complex and the 40 S-eIF-2 Met-tRNA f -GTP 43 S initiation complex. The fundamental mechanism for the inhibition is the activation of cAMP independent protein kinases that specifically phosphorylate the 38-kDa alpha-subunit of eIF-2 (eIF-2 alpha). Dephosphorylation of eIF-2 alpha accompanies the recovery of protein synthesis upon addition of hemin to inhibited heme-deficient lysates.

The heme-regulated eukaryotic initiation factor 2 alpha (eIF-2 alpha) kinase, also called heme-regulated inhibitor (HRI), plays a major role in this process. HRI is a cAMP-independent protein kinase that specifically phosphorylates the alpha subunit (eIF-2 alpha) of the eukaryotic initiation factor 2 (eIF-2). Phosphorylation of eIF-2 alpha in reticulocyte lysates results in the binding and sequestration of reversing factor RF, also designated as guanine nucleotide exchange factor or eIF-2 B, in a RF-eIF-2 (alpha P) complex; the unavailability of RF, which is required for the exchange of GTP for GDP in the recycling of eIF-2 and in the formation of the eIF-2-Met-tRNA f -GTP ternary complex, resulting in the cessation of the initiation of protein synthesis.

Although the mechanism of regulation of protein synthesis by HRI has been extensively studied, little is known about the structure and regulation of HRI itself. Chen, J. -J., et al., Proc. Natl. Acad. Sci., USA 88:315–319 (1991) previously reported the amino acid sequences of three tryptic peptides of heme-reversible HRI. HRI peptide P-52 contains the sequence -Asp-Phe-Gly-, which is the most highly conserved short stretch in conserved domain VII of protein kinases as presented by Hanks, et al., Science 241:42–52 (1988). The N-terminal 14 amino acids of HRI peptide P-74 show 50–60% identity to the conserved domain IX of kinase-related transforming proteins. These findings are consistent with the autokinase and eIF-2 alpha kinase activities of HRI. As reported by Pal et al., Biochem. 30:2555–2562 (1991), this protein appears to be erythroid-specific and antigenically different in different species.

In view of the activity and relationships of HRI to other protein kinases involved in cellular transformation, it would be advantageous to have the nucleic acid sequence encoding HRI. However, since the gene is only expressed during a very limited time period, i.e., during erythroid differentiation, and in an extremely minuscule amount, this was not a simple process. Moreover, even though three peptides isolated by tryptic digest had been sequenced, it was not clear if these were from HRI or from a contaminant of the HRI preparation. Obtaining a library containing a full length HRI cDNA is also difficult.

Chen et al. have disclosed the nucleotide sequence for DNA encoding HRI from rabbit reticulocytes. U.S. Pat. Nos. 5,690,930 and 5,525,513. However, due to differences between species, compounds which may affect the activity of the rabbit HRI may not have the same effect on human HRI. Therefore, to use HRI in humans or to identify compounds which affect the activity of human HRI, it is essential that isolated human HRI can be produced and that the sequence of human HRI is determined.

It is therefore an object of the present invention to provide a nucleic acid sequence encoding human HRI.

SUMMARY OF THE INVENTION

The present invention provides an isolated nucleic acid sequence encoding the human heme-regulated initiation factor 2 alpha kinase.

The present invention also provides a pharmaceutical composition having the heme-regulated initiation factor 2 alpha kinase in combination with a suitable pharmaceutical carrier for administration to cells.

In a further embodiment, the invention provides a method for inhibiting protein synthesis, inducing cellular differentiation, or inhibiting infection in human cells. An effective amount of a heme-regulated initiation factor 2 alpha kinase is administered to the cells.

Yet another embodiment of the invention is a method for modulating heme-regulated initiation factor 2 alpha kinase activity, by administering an effective amount of an antibody or a receptor protein which binds to heme-regulated eukaryotic initiation factor 2 alpha kinase to cells.

Another aspect of the invention is a method for determining the level of heme-regulated initiation factor 2 alpha kinase expression, by contacting a biological sample with a nucleic acid molecule which specifically binds to a gene encoding human heme-regulated initiation factor 2 alpha kinase.

BRIEF DESCRIPTION OF THE DRAWINGS

FIG. 1 shows a sequence homology comparison between the human heme-regulated initiation factor 2 alpha kinase and the related proteins from mouse, rat, and rabbit The mouse, rat, and rabbit sequences correspond to SEQ ID NOs: 3, 4, and 5, respectively.

DESCRIPTION OF THE INVENTION

The present invention provides the DNA sequence for the human gene encoding heme-regulated initiation factor 2-alpha kinase In a preferred embodiment, the gene encoding heme-regulated initiation factor 2-alpha kinase has the sequence of SEQ ID NO:1,as follows:

ggcacgaggc tagctgcagc atcggagtgt gcagtgctgg gctggccggc gggctgggct 60
gcggcccgcg cgcggccggc gatgcagggg ggcaactccg gggtccgcaa gcgcgaagag 120
gagggcgacg gggctggggc tgtggctgcg ccgccggcca tcgactttcc cgccgagggc 180
ccggaccccg aatatgacga atctgatgtt ccagcagaaa tccaggtgtt aaaagaaccc 240
ctacaacagc caaccttccc ttttgcagtt gcaaaccaac tcttgctggt ttctttgctg 300
gagcacttga gccacgtgca tgaaccaaac ccacttcgtt caagacaggt gtt-taagcta 360
ctttgccaga cgtttatcaa aatggggctg ctgtcttctt tcacttgtag tgacgagttt 420
agctcattga gactacatca caacagagct attactcact taatgaggtc tgctaaagag 480
agagttcgtc aggatccttg tgaggatatt tctcgtatcc agaaaatcag atcaagggaa 540
gtagccttgg aagcacaaac ttcacgttac ttaaatgaat ttgaagaact tgccatctta 600
ggaaaaggtg gatacggaag agtatacaag gtcaggaata aattagatgg tcagtattat 660
gcaataaaaa aaatcctgat taagggtgca actaaaccag tttgcatgaa ggtcctacgg 720
gaagtgaagg tgctggcagg tcttcagcac cccaatattg ttggctatca cacgcgtgg 780
atagaacatg ttcatgtgat tcagccacga gacagagctg ccattgagtt gccatctctg 840
gaagtgctct ccgaccagga agaggacaga gagcaatgtg gtgttaaaaa tgatgaaagt 900
agcagctcat ccattatctt tgctgagccc accccagaaa aagaaaacg ctttggagaa 960
tctgacactg aaaatcagaa taacaagtcg gtgaagtaca ccaccaattt agtcataaga 1020
gaatctggtg aacttgagtc gaccctggag ctccaggaaa atggcttggc tggtttgtct 1080
gccagttcaa ttgtgggaaca gcagctgcca ctcaggcgta attcccacct agaggagagt 1140
ttcacatcca ccgaagaatc ttccgaagaa aatgtcaact ttttgggtca gacagaggca 1200
cagtaccacc tgtatgctgca catccagatg cagctgtgtg agctctcgct gtggattgg 1260
atagtcgaga gaaacaagcg gggccgggag tatgtggacg agtctgcctg tccttatgtt 1320
atggccaatg ttgcaacaaa aatttttcaa gaattggtag aaggtgtgtt tta-catacat 1380
aacatgggaa ttgtgcaccg agatctgaag ccaagaaata tttttcttca tggc-cctgat 1440
cagcaagtaa aaataggaga ctttggtctg gcctgcacag acatcctaca gaa-gaacaca 1500
gactggacca acagaaacgg gaagagaaca ccaacacata cgtccagagt gggtacttgt 1560
ctgtacgctt caccccgaaca gttggaagga tctgagtatg atgccaagtc agatatgtac 1620
agcttggggtg tggtcctgct agagctcttt cagccgtttg gaacagaaat ggagcgagca 1680
gaagttctaa caggtttaag aactggtcag ttgccggaat ccctccgtaa aag-gtgtcca 1740
gtgcaagcca agtatatcca gcacttaacg agaaggaact catcgcagag accatctgcc 1800
attcagctgc tgcagagtga actttccaa aattctggaa atgttaacct cac-cctacag 1860
atgaagataa tagagcaaga aaaagaatt gcagaactaa agaagcagct aaacctcctt 1920
tctcaagaca aaggggtgag ggatgacgga aaggatgggg gcgtgggatg aaagtggact 1980
taacttttaa ggtagttaac tggaatgtaa attttaatc tttattaggg tatagttggt 2040
acaatgcttc gttgtattta gtaagccttt acaagacttg ttaaagatgt cagagt-gccc 2100
caagctgccg ttccttccct tcctgcccca caagctcctt ttcctgaatt tcctac-ctaa 2160
atattaacca tatgcctagt ctctgaaact aaaaacttgg acctcatcct caat-tatttt 2220
ctcctttcaa ctctgttgac cctctgtctg gtcttcctct agaaggttct accgca-gaaa 2280
ttgatgtgtg ctcccctgccc tcgtcactgc ccaagcccgg goctgcacat act-cactgga 2340
ctgttccagt ctttgacagct gccagtcttc ctgcccctt cacactgcag ctgaagttca 2400
ttacctgaag gacgcctcat catttcattc cttggctcca aaccttctgc tgc-ctctaag 2460
ataaaagctc aacttcttaa cagtgtacag tgtgcaactt ccaaccttt tatctgt-tct 2520
ctccaccttc agtttagcgt cattccaaaa ccacacccttt gcaaagcttt gtactc-cgca 2580
ccccagatga tctccaggca gctcagatct ctttcctgcc tttgccctgc actgt-tcccc 2640
ggtacttcct cctttattgt agcactcagc tccccagcca atctgtacat ccctca-gagg 2700
cagcgatctg atgaattggt ttttgaatcc cagaaaggt ctgccatgga gttg-scagtc 2760
atcacgtag atggcgtatg attttgctga atttaaata aatgaaaac cat-aaattac 2820
atgatgcttt tattgacact tgacaactgg cctaaataaa aagactctga ctctaaaaaa 2880
aaaaaaaaaa a 2891

The present invention includes fragments of the human heme-regulated initiation factor 2 alpha kinase gene or protein. Active sites of the protein can be identified by comparison to the rabbit gene which has been previously sequenced and to other kinase genes. Non-conserved regions may be altered or deleted.

Sequence comparisons are also provided which highlight areas of conserved and variable amino acids. The overall homology between the human and rabbit genes is approximately 80%. However, the homology is primarily found in highly conserved domains common to all kinases irrespective of species or type.

The invention also encompasses production of DNA sequences, or fragments thereof, which encode human heme-regulated initiation factor 2 alpha kinase and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding human heme-regulated initiation factor 2 alpha kinase or any fragment thereof. As indicated in FIG. 1, the conserved catalytic regions are known.

Also encompassed by the invention are polynucleotide sequences that are capable of hybridizing to the claimed nucleotide sequences, and in particular, those shown in SEQ ID NO:2, or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511), which are hereby incorporated by reference.

Methods for DNA sequencing are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

In another embodiment of the invention, natural, modified, or recombinant nucleic acid sequences encoding human heme-regulated initiation factor 2 alpha kinase may be ligated to a heterologous sequence to encode a fusion protein. For example, to screen peptide libraries for inhibitors of human heme-regulated initiation factor 2 alpha kinase activity, it may be useful to encode a chimeric human heme-regulated initiation factor 2 alpha kinase protein that can be recognized by a commercially available antibody. A fusion protein may also be engineered to contain a cleavage site located between the human heme-regulated initiation factor 2 alpha kinase encoding sequence and the heterologous protein sequence, so that human heme-regulated.initiation factor 2 alpha kinase may be cleaved and purified away from the heterologous moiety.

In another embodiment, sequences encoding human heme-regulated initiation factor 2 alpha kinase may be synthesized, in whole or in part, using chemical methods well known in the art (see Caruthers, M. H. et al. (1980) Nucl. Acids Res. Symp. Ser. 215–223, Hom, T. et al. (1980) Nucl. Acids Res. Symp. Ser. 225–232, which are hereby incorporated by reference). Alternatively, the protein itself may be produced using chemical methods to synthesize the amino acid sequence of human heme-regulated initiation factor 2 alpha kinase, or a fragment thereof. For example, peptide synthesis can be performed using various solid-phase techniques (Roberge, J. Y. et al. (1995) Science 269:202–204, which is hereby incorporated by reference) and automated synthesis may be achieved, for example, using the ABI 431 A Peptide Synthesizer (Perkin Elmer).

Homologous nucleotide sequences can be detected by selectively hybridizing to each other. Selectively hybridizing is used herein to mean hybridization of DNA or RNA probes from one sequence to the "homologous" sequence under stringent or non-stringent conditions (Ausubel, et al., Eds., 1989, Current Protocols in Molecular Biology, Vol. I, Greene Publishing Associates, Inc. and John Wiley & Sons, Inc., New York, at page 2.10.3, which is hereby incorporated by reference).

Methods which are well known to those skilled in the art may be used to construct expression vectors containing sequences encoding human heme-regulated initiation factor 2 alpha kinase and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., which are hereby incorporated by reference.

A variety of expression vector/host systems may be utilized to contain and express sequences encoding human heme-regulated initiation factor 2 alpha kinase. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector-enhancers, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding human heme-regulated initiation factor 2 alpha kinase, vectors based on SV40 or EBV may be used with an appropriate selectable marker.

In bacterial systems, a number of expression vectors may be selected depending upon the use intended for human heme-regulated initiation factor 2 alpha kinase. For example, when large quantities of human heme-regulated initiation factor 2 alpha kinase are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding human heme-regulated initiation factor 2 alpha kinase may be ligated into the vector in frame with sequences for the amino-terminal Met and the subsequent 7 residues of beta—galactosidase so that a hybrid protein is produced; pIN vectors (Van Heeke, G. and S. M. Schuster (1989) *J. Biol. Chem.* 264:5503–5509, which is hereby incorporated by reference); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544, which are hereby incorporated by reference.

In cases where plant expression vectors are used, the expression of sequences encoding human heme-regulated initiation factor 2 alpha kinase may be driven by any of a number of promoters. For example, viral promoters such as the 35S and 19S promoters of CAMV may be used alone or in combination with the omega leader sequence from TMV (Takamatsu, N. (1 987) *EMBO J.* 6:307–311, which is hereby incorporated by reference). Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probi. Cell Differ.* 17:85–105, which are hereby incorporated by reference). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196, which is hereby incorporated by reference).

An insect system may also be used to express human heme-regulated initiation factor 2 alpha kinase. For example, in one such system, *Autographa californica* nuclear polyhedrosis virus (AcNPV) is used as a vector to express foreign genes in *Spodoptera frugiperda* cells or in Trichoplusia larvae. The sequences encoding human heme-regulated initiation factor 2 alpha kinase may be cloned into a non-essential region of the virus, such as the polyhedrin gene, and placed under control of the polyhedrin promoter. Successful insertion of human heme-regulated initiation factor 2 alpha kinase will render the polyhedrin gene inactive and produce recombinant virus lacking coat protein. The recombinant viruses may then be used to infect, for example, *S. frugiperda* cells or Trichoplusia larvae in which human heme-regulated initiation factor 2 alpha kinase may be expressed (Engelhard, E. K. el. al. (1994) *Proc. Nat. Acad. Sci.* 91:3224–3227, which is hereby incorporated by reference).

In mammalian host cells, a number of viral-based expression systems may be utilized. In cases where an adenovirus is used as an expression vector, sequences encoding human heme-regulated initiation factor 2 alpha kinase may be ligated into an adenovirus transcription/translation complex consisting of the late promoter and tripartite leader sequence. Insertion in a non-essential E1 or E3 region of the viral genome may be used to obtain a viable virus which is capable of expressing human heme-regulated initiation factor 2 alpha kinase in infected host cells (Logan, J. and Shenk, T. (1984) *Proc. Natl. Acad. Sci.* 81:3655–3659, which is hereby incorporated by reference). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes. Specific initiation signals may also be used to achieve more efficient translation of sequences encoding human heme-regulated initiation factor 2 alpha kinase. Such signals include the ATG initiation codon and adjacent sequences. In cases where sequences encoding human heme-regulated initiation factor 2 alpha kinase, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162, which is hereby incorporated by reference).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va., 20110–2209) and may be chosen to ensure the correct modification and processing of the foreign protein.

For long-term, high-yield production of recombinant proteins, stable expression is preferred. For example, cell lines which stably express human heme-regulated initiation factor 2 alpha kinase may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

In a preferred embodiment, the gene is incorporated into a vector. Preferred vectors are viral vectors. Viral vectors include DNA viruses, such as adeno-associated virus, adenovirus, herpesvirus, such as herpes simplex virus and Epstein-Barr virus, and retroviruses, such as MoMLV. Advantageously, the retroviral vectors of the invention can integrate only into the genome of dividing cells. Thus, the vectors provide a useful vehicle for selective targeting of dividing cells. Retroviral vectors offer further advantages as there are no limitations in host range and these vectors have already been used successfully to infect many different cell types. For example, see Cepko, C., "Lineage Analysis and Immortalization of Neural Cells Via Retrovirus Vectors," in Neuromethods 16, The Humana Press, Clifton, N.J. (1989), pp. 177–219; Gilboa, E., BioEssays 5(6):252–257 (1987); Friedmann, T., Science 244.1275–1281 (1989), which are hereby incorporated by reference. One disadvantage, however, of retroviral vectors is the low production titer of the retrovirus.

In general, retroviral vectors are well known in the art. (Breakefield et al., Molec. Neuro. Biol. 1:339 (1987); Shih et al., in Vaccines 85, Cold Spring Harbor Press, Cold Spring Harbor, N.Y. (1985), pp. 177–180, which are hereby incorporated by reference). Retrovirus vectors maybe replication-defective and can be packaged into infectious retroviral particles by transfected cell lines that contain retroviral sequences coding for the proteins necessary for the packaging of retroviral RNA, but which cannot package their own RNA (Mann et al., Cell 33:153–159 (1983); Danos and Mulligan, Proc. Natl. Acad. Sci. USA 85:6460–6464 (1988), which are hereby incorporated by reference). Since retrovirus and vectors derived from them integrate into the host cell genome, their sequences are transmitted to all daughter cells. This feature of retroviruses has been successfully used for example, to trace cell lineages in the nervous system (Price et al., Proc. Natl. Acad. Sci. USA 84:156–160 (1987); Luskin et al., Neuron 1:635–647 (1988); Walsh and Cepko, Science 241:1342–1345 (1988), which are hereby incorporated by reference). Retroviruses are RNA viruses which are useful for stably incorporating genetic information into the host cell genome. When they infect cells, their RNA genomes are converted to a DNA form (by the viral enzyme reverse transcriptase). The viral DNA is efficiently integrated into the host genome, where it permanently resides, replicating along with host DNA at each cell division. This integrated provirus steadily produces viral RNA from a strong promoter located at the end of the genome (in a sequence called the long terminal repeat or LTR). This viral RNA serves both as mRNA for the production of viral proteins and as genomic RNA for new viruses. Viruses are assembled in the cytoplasm and bud from the cell membrane, usually with little effect on the cell's health. Thus, the retrovirus genome becomes a permanent part of the host cell genome, and any foreign gene placed in a retrovirus ought to be expressed in the cells indefinitely.

Retroviruses are therefore attractive vectors because they can permanently express a foreign gene in cells. Moreover, they can infect virtually every type of mammalian cell, making them exceptionally versatile. Because of their versatility, retroviruses are also the vector of choice for gene therapy in which stable integration is desired. In the design and use of retroviral vectors, the vectors usually contain a selectable marker as well as the foreign gene to be expressed. Most of the viral structural genes are gone, so these vectors cannot replicate as viruses on their own. To prepare virus stocks, cloned proviral DNA is transfected into a packaging cell. These cells usually contain an integrated provirus with all its genes intact, but lacking the sequence recognized by the packaging apparatus. Thus, the packaging provirus produces all the proteins required for packaging of viral RNA into infectious virus particles but it cannot package its own RNA. The packaging system may allow use of a variety of viral envelopes to alter viral tropism, and ability to infect human cells. Examples include retroviral vectors using amphotropic, HIV-1/2, SIV, Gibbon Ape Leukemia Virus ("GALV") or Vesicular Stomatis Virus ("VSV") envelope. The preferred vectors are MoMuLV, HIV, and SIV. Vector packaging systems and/or backbones may be derived from various sources such as MoMuLV, or even lentiviruses such as HIV-1, SIV, etc. RNA transcribed from the transfected vector is packaged into infectious virus particles and released from the cell. The resulting virus stock is termed helper-free, because it lacks wild-type replication-competent virus. This virus stock can be used to infect a target cell culture. The recombinant genome is efficiently introduced, reverse-transcribed into DNA (by reverse transcriptase deposited in the virus by the packaging cells), and integrated into the genome. Thus, the cells now express the new virally introduced gene, but they never produce any virus, because the recombinant virus genome lacks the necessary viral genes. Alternative viral vectors, which may be used in place of retroviruses to produce stable integration include the adenoassociated virus vectors ("AAV") (Flotte, et al., Gene Ther. 2, 29–37 (1995); Zeitlin, et al., Gene Ther. 2, 623–31 (1995); Baudard, et al., Hum. Gene Ther., 7, 1309–22 (1996); which are hereby incorporated by reference). For a review of retrovirus vectors, see Austin, Gene Ther. 1 Suppl 1, S6–9 (1994) and Eglitis, Blood 71, 717–22 (1988), which are hereby incorporated by reference. Other viral vectors are derived from adenovirus, herpesviruses, etc.

The present invention also provides host cells transformed with a vector carrying the human heme-regulated initiation factor 2-alpha kinase.

In another embodiment, the invention provides an isolated protein encoded by the nucleic acid molecule according to SEQ ID NO: 2., as follows:
MQGGNSGVRK REEEGDGAGA VAAPPAIDFP AEGP-
    DPEYDE SDVPAEIQVL KEPLQQPTFP 60
FAVANQLLLV SLLEHLSHVH EPNPLRSRQV
    FKLLCQTFIK MGLLSSFTCS DEFSSLRLHH 120
NRAITHLMRS AKERVRQDPC EDISRIQKIR SREVA-
    LEAQT SRYLNEFEEL AILGKGGYGR 180
VYKVRNKLDG QYYAIKKILI KGATKPVCMK
    VLREVKVLAG LQHPNIVGYH TAWIEHVHVI 240
QPRDAAIEL PSLEVLSDQE EDREQCGVKN
    DESSSSSIIF AEPTPEKEKR FGESDTENQN 300
NKSVKYTTNL VIRESGELES TLELQENGLA GLSAS-
    SIVEQ QLPLRRNSHL EESFTSTEES 360
SEENVNFLGQ TEAQYHLMLH IQMQLCELSL
    WDWIVERNKR GREYVDESAC PYVMANVATK 420
IFQELVEGVF YIHNMGIVHR DLKPRNIFLH
    GPDQQVKIGD FGLACTDILQ KNTDWTNRNG 480
KRTPTHTSRV GTCLYASPEQ LEGSEYDAKS DMYS-
    LGVVLL ELFQPFGTEM ERAEVLTGLR 540
TGQLPESLRK RCPVQAKYIQ HLTRRNSSQR
    PSAIQLLQSE LFQNSGNVNL TLQMKIIEQE 600
KEIAELKKQL NLLSQDKGVR DDGKDGGVG 629

In a preferred embodiment, the protein has heme-regulated initiation factor 2 alpha kinase activity.

Purified protein may be obtained by several methods. The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The present invention also provides antibodies to heme-regulated initiation factor 2 alpha kinase. In addition, antibody fragments, half-antibodies, hybrid derivatives, and other molecular constructs may be utilized. These antibodies and binding portions recognize and bind to the human heme-regulated initiation factor 2 alpha kinase of the present invention.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, Eur. J. Immunol. 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 ml per site at six different sites. Each injected material will contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, Antibodies: A Laboratory Manual (1988), which is hereby incorporated by reference.

In addition to utilizing whole antibodies, the processes of the present invention encompass use of binding portions of such antibodies. Such binding portions include Fab fragments, F(ab')2 fragments, and Fv fragments. These antibody fragments can be made by conventional procedures, such as proteolytic fragmentation procedures, as described in Goding, Monoclonal Antibodies: Principles and Practice, pp. 98–118, New York:Academic Press (1983), which is hereby incorporated by reference.

The invention also provides a pharmaceutical composition comprising heme-regulated initiation factor 2 alpha kinase in combination with a suitable pharmaceutical carrier for administration to cells. Preferably, the phannaceutical composition has a kinase which consists of the amino acid sequence of SEQ ID NO:2.

In yet another embodiment, the present invention provides a method for inhibiting protein synthesis, inducing cellular differentiation, or inhibiting infection in human cells. An effective amount of a heme-regulated initiation factor 2 alpha kinase is administered to cells to be treated in an effective amount and in combination with a suitable pharmaceutical carrier for administration to the cells.

The heme-regulated initiation factor 2 alpha kinase has been identified as playing a role in a number of different regulatory pathways and diseases. Raught et al. have indicated that there is a correlation between upregulation of heme-regulated initiation factor 2 alpha kinase activity in neoplastic transformation. (Raught et al., "Expression of a Translationally Regulated, Dominant-Negative CCAAT/Enhancer-Binding Protein Beta Isoform and Up-Regulation of the Eukaryotic Translation Initiation Factor 2 alpha Are Correlated with Neoplastic Transformation of Mammary Epithelial Cells," *Cancer Res* 56(19):4382–6 (1996), which is hereby incorporated by reference.) The expression of heme-regulated initiation factor 2 alpha kinase is also linked to recovery from anemia. (Uma et al., "Changes in the Expression of the Heme-Regulated eIF-2 Alpha Kinase and Heat Shock Proteins in Rabbit Reticulocytes Maturing During Recovery from Anemia," *Exp. Cell Res.* 238(1):273–82 (1998), which is hereby incorporated by reference.)

Reduced expression of a highly related kinase, RNA-activated protein kinase ("PKR"), has been found in leukemias. (Beretta et al., "Expression of the Protein Kinase PKR is Modulated by IRF-1 and is Reduced in 5q- Associated Leukemias," *Oncoyene* 12(7):1593–6 (1996), which is hereby incorporated by reference.) PKR is also associated with the control of stress-induced apoptosis and modulation of cytokine signaling. (Der et al., "A Double-Stranded RNA-Activated Protein Kinase-Dependent Pathway Mediating Stress-Induced Apoptosis," *Proc Natl Acad Sci U.S.A.* 94(7):3279–83 (1997); Kumar et al., "Deficient Cytokine Signaling in Mouse Embryo Fibroblasts with a Targeted Deletion in the PKR gene: Role of IRF-1 and NF-kappaB," *EMBO J.*, 16(2):406–16 (1997), which are hereby incorporated by reference.) Due to the similarity in function between PKR and HRI, HRI may have similar functions.

In one embodiment, an antagonist of human heme-regulated initiation factor 2 alpha kinase may be administered to a subject to prevent or treat a disorder associated with the expression of human heme-regulated initiation factor 2 alpha kinase.

In another embodiment, a vector expressing the complement of the polynucleotide encoding human heme-regulated initiation factor 2 alpha kinase may be administered to a subject to treat or prevent disorders associated with the expression of human heme-regulated initiation factor 2 alpha kinase, including, but not limited to, those described above.

An antagonist of human heme-regulated initiation factor 2 alpha kinase may be produced using methods which are generally known in the art. In particular, purified human heme-regulated initiation factor 2 alpha kinase may be used to produce antibodies or to screen libraries of pharmaceutical agents to identify those which specifically bind human heme-regulated initiation factor 2 alpha kinase.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66, which is hereby incorporated by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of human heme-regulated initiation factor 2 alpha kinase, antibodies to human heme-regulated initiation factor 2 alpha kinase, mimetics, agonists, antagonists, or inhibitors of human heme-regulated initiation factor 2 alpha kinase. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example human heme-regulated initiation factor 2 alpha kinase or fragments thereof, antibodies of human heme-regulated initiation factor 2 alpha kinase, agonists, antagonists or inhibitors of human heme-regulated initiation factor 2 alpha kinase, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In another embodiment, antibodies which specifically bind human heme-regulated initiation factor 2 alpha kinase ray be used for the diagnosis of conditions or diseases characterized by expression of human heme-regulated initiation factor 2 alpha kinase, or in assays to monitor patients being treated with human heme-regulated initiation factor 2 alpha kinase, agonists, antagonists or inhibitors. The antibodies useful for diagnostic purposes may be prepared in the same manner as those described above for therapeutics. Diagnostic assays for human heme-regulated initiation factor 2 alpha kinase include methods which utilize the antibody and a label to detect human heme-regulated initiation factor 2 alpha kinase in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring human heme-regulated initiation factor 2 alpha kinase are known in the art and provide a basis for diagnosing altered or abnormal levels of human heme-regulated initiation factor 2 alpha kinase expression. Normal or standard values for human heme-regulated initiation factor 2 alpha kinase expression are established by combining body fluids or cell extracts taken from normal mammalian subjects, preferably human, with antibody to human heme-regulated initiation factor 2 alpha kinase under conditions suitable for complex formation. The amount of standard complex formation may be quantified by various methods, but preferably by photometric means. Quantities of human heme-regulated initiation factor 2 alpha kinase expressed in subject samples, control and diseased, from biopsied tissues are compared with the standard values. Deviation between standard and subject values establishes the parameters for diagnosing disease.

In another embodiment of the invention, the polynucleotides encoding human heme-regulated initiation factor 2 alpha kinase may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of human heme-regulated initiation factor 2 alpha kinase may be correlated with disease. The diagnostic assay may be used to distinguish between absence, presence, and excess expression of human heme-regulated initiation factor 2 alpha kinase, and to monitor regulation of human heme-regulated initiation factor 2 alpha kinase levels during therapeutic intervention.

In a further embodiment, the invention provides a method for inhibiting protein synthesis, inducing cellular differentiation, or inhibiting infection in human cells. An effective amount of a heme-regulated initiation factor 2 alpha kinase is administered to the cells.

Yet another embodiment of the invention is a method for modulating heme-regulated initiation factor 2 alpha kinase activity, by administering an effective amount of an antibody or a receptor protein which binds to heme-regulated eukaryotic initiation factor 2 alpha kinase to cells.

The protein of the present invention may also be used as a drug screening target. Specifically, the HRI protein may be used to identify compounds which can either increase or decrease kinase activity. In one embodiment, the kinase activity can be assayed by labelling the target peptide sequence (eIF2-alpha, HRI or fragments thereof) with ($^{32}$P), carrying out the kinase reaction (with or without a compound to be screened), and analyzing the phosphorylated protein by SDS-PAGE and autoradiography. (Chefalo et al., "Heme-Regulated eIF-2 Alpha Kinase Purifies as a Hemoprotein.," Eur. J. Biochem., 258(2):820–30 (1998); Berlanga et al., "Characterization of the Hemin-Sensitive Eukaryotic Initiation Factor 2 alpha Kinase from Mouse Nonerythroid Cells," J Biol. Chem., 273(48):32340–6 (1998), which are hereby incorporated by reference.) Alternative methods include the non-radioactive assays. For example, the target peptide can be labeled with a fluorescent tag (such as the one described in U.S. Pat. No. 5,580,747). After the kinase reaction, the phosphorylated protein can be analyzed by SDS-PAGE and image analysis.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated nucleic acid molecule comprising:
   a nucleic acid sequence according to SEQ ID NO:1;
   a nucleic acid sequence which encodes the amino acid sequence according to SEQ ID NO:2; or
   a nucleic acid molecule having at least 90% amino acid sequence identity to a nucleic acid sequence according to SEQ ID NO:1 wherein the nucleic acid molecule encodes a protein having heme-regulated initiation factor 2 alpha kinase activity.

2. A vector comprising the nucleic acid molecule according to claim 1.

3. The vector according to claim 2, wherein the vector is a virus.

4. The vector according to claim 3, wherein the vector is a DNA virus.

5. The vector according to claim 4, wherein the DNA virus is selected from the group consisting of adeno-associated virus, adenovirus, and herpesvirus.

6. The vector according to claim 2, wherein the virus is a retrovirus.

7. The vector according to claim 6, wherein the retrovirus is selected from the group consisting of MoMLV, HIV-1, and SIV.

8. A host cell transformed with the vector according to claim 2.

9. A method for detecting the presence of heme-regulated initiation factor 2 alpha kinase expression in a biological sample, comprising:
   contacting the biological sample with a nucleic acid molecule comprising SEQ ID NO:1 as a probe in a nucleic acid hybridization assay; and
   detecting whether the nucleic acid molecule has undergone any hybridization, thereby indicating the presence of heme-regulated initiation factor 2 alpha kinase expression in the biological sample.

10. A method according to claim 9, wherein the nucleic acid molecule is selected from the group consisting of oligonucleotide sequences, complementary DNA and RNA, and peptide nucleic acids.

11. A method according to claim 9 further comprising:
    quantitating heme-regulated initiation factor 2 alpha kinase expression in a biological sample.

* * * * *